(12) United States Patent
Fusejima et al.

(10) Patent No.: US 6,171,619 B1
(45) Date of Patent: Jan. 9, 2001

(54) SPHERICAL GRANULE, PROCESS FOR PRODUCING THE SAME, AND SPHERICAL GRANULE PREPARATIONS USING THE SAME

(75) Inventors: Yasutoyo Fusejima; Yasuhiro Takemura; Nagayoshi Myo; Hisayoshi Kato, all of Tokyo (JP)

(73) Assignee: Freund Industrial Co., Ltd., Tokyo (JP)

( * ) Notice: Under 35 U.S.C. 154(b), the term of this patent shall be extended for 0 days.

(21) Appl. No.: 09/254,438

(22) PCT Filed: Sep. 5, 1997

(86) PCT No.: PCT/JP97/03134

§ 371 Date: Mar. 9, 1999

§ 102(e) Date: Mar. 9, 1999

(87) PCT Pub. No.: WO98/10751

PCT Pub. Date: Mar. 19, 1998

(30) Foreign Application Priority Data

Sep. 10, 1996 (JP) .................................................. 8-260167
Jul. 31, 1997 (JP) .................................................. 9-218989

(51) Int. Cl.[7] .................................................. A61K 9/14
(52) U.S. Cl. .................................................. 424/489
(58) Field of Search .................................................. 424/489

(56) References Cited

U.S. PATENT DOCUMENTS 5,516,531 * 5/1996 Makino et al. ...................... 424/494

FOREIGN PATENT DOCUMENTS 62-269739 * 11/1987 (JP) .
63-23731 * 2/1988 (JP) .

(List continued on next page.)

OTHER PUBLICATIONS

Mizunaga et al.; "Summary of the Lectures Presented at the 7th Symposium on Particulate Preparations and Designs"; Oct. 1990; pp. 89–93.*
Sakamoto; "Summary of the Lectures Presented at the 7th Symposium on Particulate Preparations and Designs"; Oct. 1990; pp. 118–121.*

(List continued on next page.)

Primary Examiner—S. Mark Clardy
Assistant Examiner—Konata M. George
(74) Attorney, Agent, or Firm—Foley & Lardner

(57) ABSTRACT

The invention relates to spherical granules having a uniform grain size and a uniform density which are suitable for a controlled-release preparation, a process for producing the same, and a spherical granule preparation using the same.

Specifically, the invention relates to a process for producing spherical granules comprising the steps of: wetting powder materials comprising one or more kinds of pharmaceutical substances and have a mean particle size of from 1 to 100 $\mu$m; charging the wet powder materials into a centrifugal fluidized granulating apparatus; spraying a liquid to the wet powder materials at a rate of less than 3% based on the plastic limit of the powder materials per min. while rotating the rotary disk of the centrifugal fluidized granulating apparatus until the liquid content of the powder materials reaches 75 to 120% based on the plastic limit of the powder materials, and drying the sprayed product to give spherical granules; spherical granules having a mean grain size of 100–1000 $\mu$m, in which at least 90% by weight of the total amount of the spherical granules has such a grain size distribution that the maximum grain size is not larger than 1.2 times the minimum grain size, and the difference in density between the individual spherical granules is less than 0.05 g/cm$^3$; and a spherical granule preparation comprising the spherical granules.

3 Claims, 1 Drawing Sheet

FOREIGN PATENT DOCUMENTS

| | | | |
|---|---|---|---|
| 4-283520 | * | 10/1992 | (JP) . |
| 5-92918 | * | 4/1993 | (JP) . |
| 05229961 | * | 9/1993 | (JP) . |
| 5-229961 | * | 9/1993 | (JP) . |
| 6-205959 | * | 7/1994 | (JP) . |
| 7-2761 | * | 1/1995 | (JP) . |
| 7-173050 | * | 7/1995 | (JP) . |

OTHER PUBLICATIONS

Gajdos; "Rotorgranulatoren—Verfahrenstechnische Bewertung der Pelletherstellung mit Hilfe der faktoriellen Versuchsplanung", Pharm. Ind.; vol. 45, No. 7; 1983; pp. 722–728.*

Funakoshi; "Compressive Molding and Granulation of Medicines"; Aug. 4, 1976; p. 114.*

* cited by examiner

SPHERICAL GRANULE, PROCESS FOR PRODUCING THE SAME, AND SPHERICAL GRANULE PREPARATIONS USING THE SAME

FIELD OF THE INVENTION

The present invention relates to spherical granules having a uniform grain size and a uniform density, which are suitable for controlled-release preparations.

DESCRIPTION OF THE RELATED ART

Recently, drug delivery systems (DDS) have been studied intensively and some of them are now put into actual use. The release control for oral dosage form is major one of such DDSs. The dosage forms utilizing the release control techniques are classified into two categories: single unit type and multiple unit type. These two dosage forms have inherent characteristics of their own. However, multiple unit type dosage is superior in view of ease of and high degree flexibility in drug design. There are many types of the multiple unit dosage form and most of them utilize plurality kinds of granules each imparted with predetermined diffusion properties as the constituents.

The granules of such multiple unit dosage form can generally be prepared by coating a medicinal ingredient (i.e., a pharmaceutically active ingredient) and a release control agent onto spherical granules with a grain size of about 200–1000 $\mu$m made of inert substances such as sucrose, starch and microcrystalline cellulose. As the spherical granules made of inert substances, commercial products sold under the trade name of, for example, "NONPAREIL" (Freund Industrial Co., Ltd.) and "Celpher" (Asahi Chemical Industry Co., Ltd.) are available, which are useful products as the raw materials for medicines. However, these products still have plenty of room for improvement.

That is, the spherical granules are required to have a coating layer on the surface which is capable of imparting a desired diffusion behavior to the medicinal ingredient. In addition, the spherical granules must satisfy many other requirements, including preciseness of the coating layer formation, less variation in lots of the spherical granules, ease of measuring and filling and no segregation during processing. The factors required for the spherical granules themselves which may affect the above-mentioned requirements include grain size, hardness, degree of abrasion wear, degree of spherisity, solubility and water-absorbing capacity. The factors required for the aggregates of the spherical granules include grain distribution, bulk density and angle of repose. In order to modify these factors, there are proposed several means.

With respect to the physical properties of the spherical granules such as hardness, degree of abrasion wear, solubility, water-absorbing capacity, the types of the constituent substances of the spherical granule is a predominant factor, and there have been made a number of studies on the constituents. For example, Japanese Unexamined Patent Publication No. 6-205959 proposes a composition comprising at least 95% by weight of lactose; Japanese Unexamined Patent Publication No. 4-283520 proposes a composition comprising 10–70% of crystalline cellulose having a mean polymerization degree of 60–375 and 10–90% of water-soluble additives; and Japanese Unexamined Patent Publication No. 7-173050 proposes a composition comprising at least 50% of crystalline cellulose having a mean polymerization degree of 60–375. Japanese Unexamined Patent Publication No. 5-229961 discloses a composition comprising mainly lactose and cellulose; and Japanese Patent Publication No. 7-2761 discloses a composition comprising at least 20% of microcrystalline cellulose. These compositions are closely correlated with the apparatus and the process employed for producing the spherical granules.

On the other hand, among the properties mentioned above, the universal properties independent on the types of the constituent substances include grain size and grain size distribution.

With respect to grain size, Japanese Patent Publication No. 7-2761, supra, discloses spherical granules in which at least 90% has a fraction falling through a 24 mesh (710 $\mu$m); and Japanese Unexamined Patent Publication No. 5-92918 discloses spherical granules which give a grain size of not greater than 500 $\mu$m when coated with a medicinal ingredient, both which are described to be good because they meet the requirements of the Japanese Pharmacopoeia and can reduce the variations in preparation.

With respect to grain size distribution, it is described in, for example, Mizunaga et al., "Summary of the lectures presented at the 7th Symposium on Preparation and Particle Design", pp. 89–93, October 1990, that (although not referred to the spherical granules per se) granules comprising a medicinal ingredient and the like coated onto spherical granules, which are spherical in shape and have a sharp grain size distribution, are preferable in view of efficiency and reproducibility of the coating to the spherical granules.

However, in this publication, we cannot find any date showing the relationship between the grain size distribution and the coating efficiency or any description referring to what grain size distribution is preferable for pharmaceutical granule preparations.

There are several publications referring to the grain size distribution of the granulated spherical granules, such as a thesis for a degree cataloged in the National Diet Library by Funakoshi., "Compressive Molding and Granulation of Medicines", Aug. 4, 1976, p.114; Sakamoto, "Summary of the lectures presented at the 7th Symposium on Preparation and Particle Design", pp. 118–121, October 1990; B. Gajdos, Pharm. Ind., 45, No.7, pp.722–728, 1983; and Japanese Unexamined Patent Publication No. 62-269739. However, in these publications, such a sharp grain size distribution as required for the spherical granules of the present invention cannot be attained, and there is no description referring to the difference in density of the spherical granules and what result can be obtained by the use of the spherical granules for preparing pharmaceutical preparations.

As a method for producing spherical granules having a sharp grain size distribution, Japanese Unexamined Patent Publication No. 63-23731 discloses a process in which raw materials are charged into a rotary granulator successively and the resultant product is discharged continuously. Although this process has the advantage of continuous production, it is not clear what type of grain size distribution the granules actually have. In the specification of this publication, we can found only the portion "when the grain size distribution range (attained by such continuous discharge process) which is already extremely good should be more improve to, for example, 1.0–1.2 mm, . . . continuous feeding into a sizing apparatus may be available", and there is no description referring to the grain size distribution. In addition, this process merely classifies the granules to desired grain sizes by sieving. However, sieving of spherical granules sometimes results in poor efficacy of classification under a certain grain size distribution of the raw powder materials and, consequently, results in production of a granules containing many fractions falling through the sieve and a poor yield, which being not suitable for practical application.

Japanese Unexamined Patent Publication No. 6-205959, supra, also discloses the incorporation of medicinal ingredients into the spherical granules. However, such medicinal ingredient-containing spherical granules also do not show a sharp grain size distribution.

As discussed above, in order to produce a controlled-release pharmaceutical preparation of multiple unit dosage form, it has already been practiced and studied on coating a medicinal ingredient and a release control agent onto spherical granules or incorporating a medicinal ingredient into spherical granules. However, it is hard to say that the conditions necessary for imparting an intended diffusion behavior to the spherical granules is well elucidated. Particularly with respect to the universal physical properties independent on the types of the components, any effective proposal has not been made.

In controlled-release preparations comprising spherical granules, it is considered to be the most essential properties that each granule shows a same and uniform diffusion pattern and that there is no variation in measuring and filling. These properties depend on the above-mentioned universal physical properties. When the spherical granules prepared by a conventional process or commercially available spherical granules are used, such variations can not be reduced to a level below a certain level. Therefore, in the prior art, the spherical granulation preparation should be designed in contemplation of these problems in consideration of such drawbacks.

The spherical granules containing a medicinal ingredient is also required to have less variation in measuring or filling. The medicinal ingredient-containing spherical granules are advantageous over the spherical granules coated with a medicinal ingredient. This is because that the former spherical granules can contain a larger amount of the medicinal ingredient per weight compared to the latter spherical granules and, therefore, can be filled into a smaller capsule and are easy to be swallowed. Therefore, the spherical granules are considered to be useful for the rising geriatric medicine problem. In order to address this problem, it is necessary to prepare spherical granules having a sharp grain size distribution and show less variation in filling into a capsule or the like.

Accordingly, the object of the present invention is to reduce such variation and improve the release controlling properties of controlled-release preparations.

DISCLOSURE OF THE INVENTION

The present invention relates to spherical granules comprising one or more kinds of pharmaceutical substances, which have a mean grain size of from 100 to 1000 $\mu$m, wherein at least 90% by weight of the total amount of the spherical granules has such a grain size distribution that the maximum grain size is not larger than 1.2 times the minimum grain size, and wherein the difference in density between the individual spherical granules is less than 0.05 g/cm$^3$; where the pharmaceutical substances may be comprised of only non-medicinal ingredients or may contain a medicinal ingredient.

The present invention also relates to a process for producing spherical granules comprising the steps of: wetting powder materials comprising one or more kinds of pharmaceutical substances and have a mean particle size of from 1 to 100 $\mu$m; charging the wet powder materials into a centrifugal fluidized granulating apparatus; spraying a liquid to the wet powder materials at a rate of less than 3% based on the plastic limit of the powder materials per min. while rotating the rotary disk of the centrifugal tumbling granulating apparatus until the liquid content of the powder materials reaches 75 to 120% based on the plastic limit of the powder materials; and drying the sprayed product to give spherical granules.

The present invention also relates to a spherical granule preparation comprising a medicinal ingredient and/or a coating film-forming ingredient both coated onto the spherical granules claimed; where the coating film-forming ingredient may be a release control agent for the medicinal ingredient.

BEST MODE FOR CARRYING OUT THE INVENTION

Figure 1:
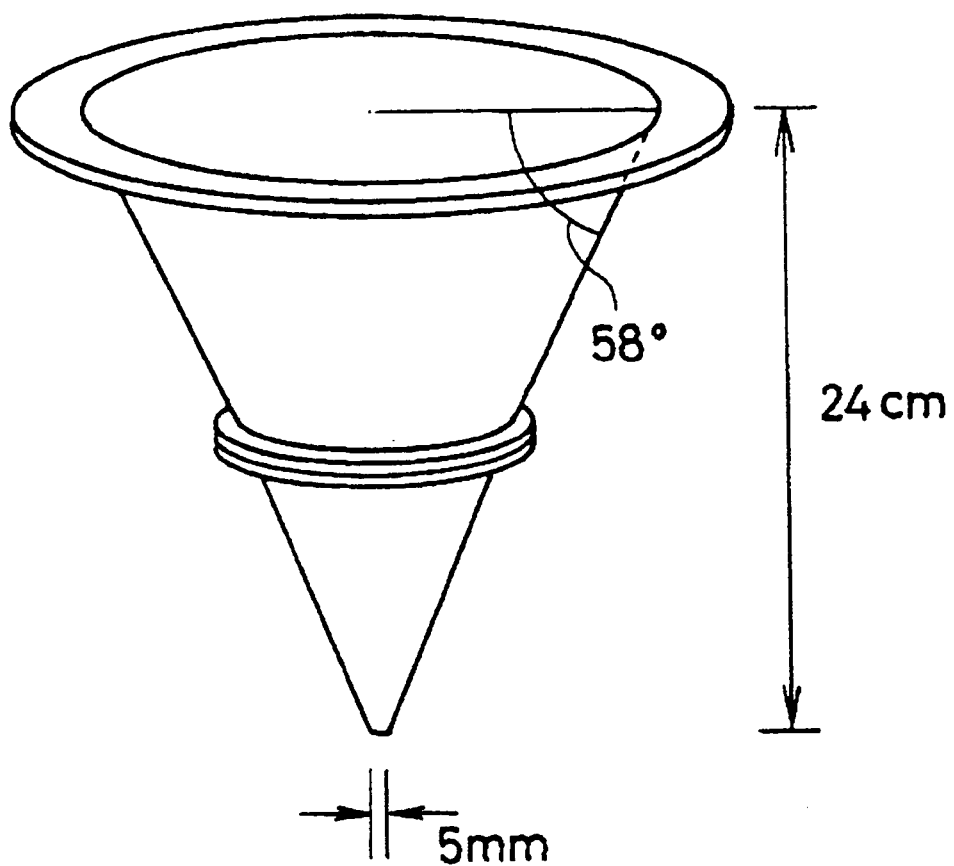
FIG. 1 illustrates a hopper that is used for analysis of the time-dependent variation of acetaminophen content in coated spherical granules.

The mean grain size of the spherical granules used in the present invention is within the range of 100–1000 $\mu$m. With the mean grain size of less than 100 $\mu$m, it is difficult to control the release of the medicinal ingredient. Whereas with the mean grain size of larger than 1000 $\mu$m, variation in filling is likely to become large and the surface area per weight becomes small; therefore, if the medicinal ingredient is present in the coating layer, the weight of the resultant spherical granule preparation based on the weight of the medicinal ingredient becomes undesirably large. Accordingly, the mean grain size falling outside of the range is not preferable.

In order to reduce the variation in release of the medicinal ingredient from the controlled-release preparation, it is required that the preparation comprise the spherical granules in which at least 90% by weight of the total amount of the granules has such a grain size distribution that the maximum grain size is less than 1.2 times the minimum grain size and the difference in density of the individual spherical granules is less than 0.05 g/cm$^3$. By using the aggregate of the spherical granules having such properties, it becomes possible to prevent segregation during, for example, coating the medicinal ingredient onto the spherical granules, transportation of the coated granules and discharging the coated spherical granules from a hopper, to coat the spherical granules in a uniform thickness, and to prevent the variations during measuring and filling.

For the production of such spherical granules, conventional processes are not suitable, such as those in which powder materials are deposited onto core materials and then granulate the resultant materials and those in which cylindrical granules obtained by compression granulation are spheronized by centrifugal rolling. This is because the former process causes the difference in density between the core and the powder-deposited layer so that the granules each having a different weight ratio between the core and the deposited powder materials show a different density, and the latter process can not provide spherical granules having a sharp grain size distribution.

The granulation method suitable for the present invention is a method disclosed in the above-cited Japanese Unexamined Patent Publication No. 5-229961 in which the conditions are further restricted.

That is, it is required for the raw powder materials used in the present invention to have a mean particle size of from 1 to 100 μm. If the particle size is smaller than 1 μm, dusting and adhesion of the powder materials are likely to occur, resulting in inconvenient handling. In addition, there is no advantage in use of such fine powder. Whereas if the mean particle size is larger than 100 μm, the surface roughness of the produced granules is likely to become large. Therefore, the mean particle size falling outside the range is not preferable.

The amount of the liquid added to the powder materials (in the case of a mix solution of two or more kinds of liquids each having a different boiling point, it means the amount of the liquid remaining at the end of the granulation step) is 75–120% based on the plastic limit of the powder materials. It is necessary to use the liquid in a larger amount based on the plastic limit with increasing the intended grain size of the granulated product; thus, the grain size of the product can be controlled. In this instance, the rate of addition of the liquid largely affects the grain size distribution of the product. Accordingly, in order to attain a good grain size distribution, the rate should be set to 3% or less, preferably 2% or less, based on the plastic limit of the powder materials per min., in terms of the rate of addition of the liquid remaining at the end of the granulating process. In the prior processes, the rate is high, for example, 5.3%, 3.2% and 4.0% based on the plastic limit per min. respectively described in Examples 1, 2 and 3 of Japanese Unexamined Patent Publication No. 5-229961, supra, in which all of the resultant spherical granules showed wide grain size distributions.

The spherical granule preparation of the present invention may be formulated into any dosage form depending on the intended application. For example, the spherical granules consisting of non-medicinal ingredients alone may be coated with both a medicinal ingredient and a coating film-forming ingredient; the spherical granules containing a medicinal ingredient may be coated with a coating film-forming ingredient; or the spherical granules containing a first medicinal ingredient may be coated with both a second medicinal ingredient which may be same as or different from the first medicinal ingredient and a coating film-forming ingredient. When both a medicinal ingredient and a coating film-forming ingredient are coated onto the spherical granules, these ingredients are pre-mixed to form a coating layer or, alternatively, the medicinal ingredient is first coated onto the spherical granules as an inner coating layer and the coating film-forming ingredient is then coated thereonto as an outer coating layer, thereby forming a double layered coating structure. Any of these methods may be employed.

Examples of the non-medicinal ingredient used in the spherical granule preparation of the present invention include, but not limited to, lactose, starch, microcrystalline cellulose, powder cellulose, hardened oil and waxes. When a medicinal ingredient is incorporated into spherical granules, any type of medicinal ingredient may be used, including those which is water-soluble, oil-soluble, or slightly soluble to both water and oil. The spherical granule preparation of the present invention may further contain auxiliary agents such as a release control agent (e.g., a matrix forming agent), an inclusion agent, a non-crystallizing agent (e.g., a solid solution forming agent), a penetrating agent, a dissolution enhancing agent, a pH adjusting agent and a stabilizer.

In the process for producing the spherical granules of the present invention, the raw powder materials are wetted generally with water or a liquid solution mainly composed of water. The amount of the liquid used for wetting is 35–75%, preferably 40–70%, based on the plastic limit of the powder materials.

The liquid is preferably added in a larger amount if the intended grain size of the spherical granules is larger, and added in a smaller amount if the intended grain size of the granules is smaller. However, the grain size is ultimately controlled by varying the total amount of the liquid used as mentioned below, and the amount of the liquid added in this step is merely an adjunctive control factor for the grain size.

The rate of addition of the liquid does not have a particular lower limit in view of the physical properties of the granulated spherical granules. However, if the rate is too low, the process becomes much too time-consuming and, therefore, the cost for manufacture becomes expensive, which being not suitable for practical application. If the rate is extremely too low, remarkable improvement in physical properties cannot be attained. For these reasons, the rate of addition of the liquid is generally not less than 0.05%, preferably not less than 0.1%, based on the plastic limit of the powder materials per min.

For this wetting procedure, any apparatus may be available, such as a ribbon blender, a kneader and a high speed mixer.

The centrifugal fluidized granulating apparatus used in the present invention may be an apparatus having a cylindrical can-type body equipped with a surface-smoothed rotary disc at the bottom part of the can-type body and a spraying means at the upper part of the rotary disk, in which air is fed through the gap between the end of the rotary disk and the can-type body to prevent the granules from falling through the gap and to facilitate the fluidizing, mixing and drying of the granules. As such apparatus, CF Granulator manufactured by Freund Industrial Co., Ltd. may be available, for example. However, other type of apparatus in which the shape and the surface unevenness of the rotary disk and equipment of other members such as a mixing means (e.g., a baffle) are different from the above-mentioned apparatus may also be available, as long as it has a similar function as the above-mentioned apparatus.

The number of revolutions of the rotary disk may vary depending on the size of the apparatus, and is generally 20–400 RPM, preferably 40–300 RPM.

The liquid sprayed onto the powder materials is not particularly limited and any one may be used, such as water, a volatile liquid (e.g., ethanol, methanol, ethyl acetate, methyl acetate, acetone) and a non-volatile liquid (e.g., ethylene glycol, propylene glycol, glycerol), preferably a liquid solution comprising water or a non-volatile liquid. The liquid may also contain a binder such as hydroxypropyl cellulose, hydroxypropylmethyl cellulose, polyvinylpyrrolidone, pullulan, gum arabic and hemicellulose. However, it is generally preferable to use water alone or a mix solution comprising water as one component.

The liquid is added in such an amount that the liquid content in the resultant spherical granules becomes 75–120% based on the plastic limit of the raw powder materials. With respect to the plastic limit, it is described in detail in Funakoshi "Compressive Molding and Granulation of Medicines", supra. According to the description in this paper, the optimum amount of water added is 55–65% based on the plastic limit of the powder materials. In contrast, Japanese Unexamined Patent Publication No. 5-229961 describes that the water content is preferably 95–110% based on the plastic limit of the powder materials.

In the present invention, by employing the rate of addition of the liquid of less than 3% based on the plastic limit of the powder materials per min., it becomes possible to attain a sharp grain size distribution of the spherical granules and also becomes possible to increase the final liquid content of the spherical granules to the range of 75–120% based on the plastic limit of the powder materials; thus facilitating the control of the grain size of the spherical granules.

Here, with respect to the ratio between the amount of the liquid added and the plastic limit of the powder materials, the amount of the liquid means the amount of the liquid remaining at the end of the granulation process. Therefore, if a liquid mixture containing a volatile liquid is used, the ratio is calculated on the assumption that the volatile liquid does not remain at the end of the granulation process.

In the process of the present invention, the spherical granules yielded after the granulation process are appropriately dried to give a final product. For drying the spherical granules, any type of drying apparatus is available, such as a fluidized bed-type apparatus and a tray dryer.

The spherical granules of the present invention can be principally prepared only by the above-mentioned granulation process. However, if necessary, after drying, the spherical granules may be put through a sieve to give a final product. According to the present invention, since a sharp grain size distribution of the spherical granules can be attained, the efficiency of sieving increases and the amount of the granules falling through the sieve decreases; whereby spherical granules containing 90% or more of the granules falling within the intended grain size range can be obtained easily.

In the present invention, any type of medicinal ingredient can be coated onto the spherical granules to obtain a spherical granule preparation. As the coating film-forming ingredients, examples include a water-soluble polymer such as hydroxypropyl cellulose, hydroxypropylmethyl cellulose, pullulan, gum arabic, hemicellulose, polyvinylpyrrolidone and polyvinyl alcohol); a release control agent such as an enteric polymer, e.g., hydroxypropylmethyl cellulose phthalate, hidroxypropylmethyl cellulose acetate succinate, carboxymethylethyl cellulose, cellulose acetate phthalate and a methacrylate-based copolymer, and a slightly soluble polymer such as shellac and ethyl cellulose; or a mixture of any of the foregoing.

The spherical granules containing a medicinal ingredient or the spherical granules coated with a medicinal ingredient on the surface according to the present invention may be used per se as a pharmaceutical preparation. Alternatively, they may be filled into a capsule or subjected to compressive molding with a suitable excipient to form a pharmaceutical preparation. Among these pharmaceutical preparations, those comprising the spherical granules containing a medicinal ingredient is advantageous. This is because such spherical granules can contain a larger amount of a medicinal ingredient per weight than those prepared by the conventional process in which a medicinal ingredient is incorporated into the coating layer and, further more, can be prepared into a smaller capsule or tablet, leading an ease of administration.

EXAMPLE 1

A mixture of 1400 g of lactose (DMV Co.) according to the Japanese Pharmacopoeia (DMV CO.) having a mean particle size of 20 µm and 600 g of crystalline cellulose (AVICEL® PH-101; Asahi Chemical Industry Co., Ltd.) according to the Japanese Pharmacopoeia having a mean particle size of 40 µm was charged into a kneader, and 650 ml of water was added thereto. The mixture was kneaded for 20 min. (at this point in time, the water content was 65.7% based on the plastic limit of the powder materials). The resultant mixture was charged into a centrifugal fluidized granulator CF-360 Model (Freund Industrial Co., Ltd.) and then 500 ml of water-containing ethanol having an ethanol content of 25% by weight was sprayed thereonto over 25 min. while rotating the rotary disk at 200 RPM. The resultant powder product had a water content of 103.5% based on the plastic limit of the powder materials. Therefore, the rate of spraying water to the powder materials was 1.51% based on the plastic limit of the powder materials per min. The spherical granules thus obtained were subjected to fluidized drying (by fluidized-bed, etc.). The dried spherical granules had a fraction falling through a 425 µm sieve of 0.7%, a fraction of 425–500 µm of 92.2% and a fraction remaining on a 500 µm sieve of 7.1%, and a density as measured on 20 granules of 1.454 g/cm$^3$ at the maximum and 1.427 g/cm$^3$ at the minimum (the difference between the maximum and the minimum densities was 0.027 g/cm$^3$). The measurement of density was performed by sink-float density determination method using carbon tetrachloride and methylene chloride.

EXAMPLE 2

A mixture of 1000 g of lactose according to the Japanese Pharmacopoeia (DMV Co.) having a mean particle size of 10 µm and 1000 g of AVICEL® PH-101, supra, having a mean particle size of 40 µm was charged into a ribbon blender, and 600 ml of water was added thereto. The mixture was stirred for 30 min. (at this point in time, the water content was 42.6% based on the plastic limit of the powder materials). The resultant mixture was charged into a centrifugal fluidized granulator CF-360 Model and then 750 ml of water-containing ethanol having an ethanol content of 30% by weight was sprayed thereonto over 35 min. while rotating the rotary disk at 200 RPM. The resultant powder product had a water content of 79.8% based on the plastic limit of the powder materials. Therefore, the rate of spraying water to the powder materials was 1.06% based on the plastic limit of the powder materials per min. The spherical granules thus obtained were subjected to tray drying. The dried spherical granules had a fraction falling through a 250 µm sieve of 2.3%, a fraction of 250–300 µm of 90.7% and a fraction remaining on a 300 µm sieve of 7.0%, and a density as measured on 20 granules of 1.459 g/cm$^3$ at the maximum and 1.428 g/cm$^3$ at the minimum (the difference between the maximum and the minimum densities was 0.031 g/cm$^3$).

COMPARATIVE EXAMPLE 1

Substantially the same procedure as in Example 1 was conducted, except that 600 ml of water-containing ethanol was sprayed over 8 min., thereby producing spherical granules. The rate of spraying water to the powder materials was 5.7% based on the plastic limit of the powder materials per min. The dried spherical granules had a fraction falling through a 425 µm sieve of 1.3%, a fraction of 425–500 µm of 71.0% and a fraction remaining on a 500 µm sieve of 27.7%, and a density as measured on 20 granules of 1.473 g/cm$^3$ at the maximum and 1.425 g/cm$^3$ at the minimum (the difference between the maximum and the minimum densities was 0.048 g/cm$^3$).

COMPARATIVE EXAMPLE 2

Substantially the same procedure as in Example 1 was conducted, except that lactose having a mean particle size of 120 µm was used, thereby producing spherical granules.

Since the resultant spherical granules had a very rough surface, they were not suitable for preparation of pharmaceutical preparations.

COMPARATIVE EXAMPLE 3

A commercially available product NONPAREIL® 103 (Freund Industrial Co., Ltd.; spherical granules comprising sucrose crystal cores and sucrose powder bound onto the cores with a sucrose syrup) was further subjected to sieving to give a fraction of 500–600 µm. The density as measured on 20 granules of the fraction was 1.559 g/cm$^3$ at the maximum and 1.506 g/cm$^3$ at the minimum (the difference between the maximum and the minimum densities was 0.053 g/cm$^3$).

EXAMPLE 3

To a powder mixture of 1200 g of ascorbic acid (the measured plastic limit value: 0.17g/cm$^3$) and 800 g of AVICEL® PH-101, supra, was charged into a ribbon blender, was added 750 ml of water. The mixture was kneaded in a ribbon blender for 15 min. (at this point in time, the water content was 63.1% based on the plastic limit of the powder materials). The resultant wet powder mixture (2000 g) was charged into a centrifugal fluidized granulator CF-360 Model and then 240 ml of water was sprayed thereonto over 20 min. while rotating the rotary disk at 180 RPM. The resultant powder product had a water content of 91% based on the plastic limit of the powder materials. Therefore, the rate of spraying water to the powder materials was 1.39% based on the plastic limit of the powder materials per min. The spherical granules thus obtained were subjected to fluidization drying. The dried spherical granules had a fraction falling through a 710 µm sieve of 0.5%, a fraction of 710–850 µm of 91.2% and a fraction remaining on a 850 µm sieve of 8.3%, and a density as measured on 20 granules of 1.421 g/cm$^3$ at the maximum and 1.383 g/cm$^3$ at the minimum (the difference between the maximum and the minimum densities was 0.038 g/cm$^3$).

EXAMPLE 4

The spherical granules (1 kg) prepared by the procedure of Example 1 were charged into a centrifugal fluidized granulator CF-360 Model, and then 520 g of a 5% aqueous solution of hydroxypropyl cellulose HPC-L (Nippon Soda Co., Ltd.) was sprayed thereonto over 50 min. while rotating the rotary disk at 200 RPM and spreading a power mixture of 300 g of acetaminophen, 300 g of cornstarch and 400 g of the above-defined lactose, thereby preparing an acetaminophen-coated spherical granules. The resultant spherical granules were put through a 600 µm sieve. The fraction remaining on the sieve had an acetaminophen content of 14.2%, and the fraction falling through the sieve had an acetaminophen content of 12.4%.

COMPARATIVE EXAMPLE 4

Substantially the same procedure as in Example 4 was conducted, except that a commercially available product NONPALEL 105 (Freund Industrial Co., Ltd.) with a grain size of 355–500 µm (the product had the same composition as the spherical granules obtained in Comparative Example 1, and was prepared at the same water spraying rate as that in Comparative Example 1) was used, thereby producing spherical granules. The resultant spherical granules were put through a 500 µm sieve. The fraction remaining on the sieve had an acetaminophen content of 15.2% and the fraction falling through the sieve had an acetaminophen content of 12.2%. The fraction remaining on the 500 µm sieve was further put a 600 µm sieve. The fraction remaining on the sieve had an acetaminophen content of 16.3%.

When the present Comparative Example 1 and Example 4 in which the spherical granules of the present invention were used were compared to each other, it was found that the product of Example 4 had a more uniform acetaminophen content.

COMPARATIVE EXAMPLE 5

Substantially the same procedure as in Example 4 was conducted, except that the fraction obtained by the re-sieving in Comparative Example 3 was used, thereby producing acetaminophen-coated spherical granules. The resultant spherical granules were put through a 710 µm sieve. The fraction remaining on the sieve had an acetaminophen content of 14.9% and the fraction falling through the sieve had an acetaminophen content of 12.1%.

As a result, it was found that even if the spherical granules had a sharp grain size distribution, the spherical granule preparation had a non-uniform acetaminophen content if the densities of the individual spherical granules were different.

EXAMPLE 5

Substantially the same procedure as in Example 1 was conducted, except that powdered cellulose (W-300G, Nippon Paper Industries Co., Ltd.) having a mean particle size of about 30 µm was used in place of AVICEL® and 1100 ml of water-containing ethanol was sprayed over 50 min., thereby producing spherical granules. The water content of the mixture charged into CF-360 was 51.1% based on the plastic limit of the powder materials and the water content of the spherical granules at the end of the granulation process was 116.0% based on the plastic limit of the powder materials. The rate of spraying water was 0.97% based on the plastic limit of the powder materials per min. Although the plastic limit of the powder cellulose was difficult to be determined, it was determined to be 1.70 by averaging five measurements. The resultant spherical granules had a fraction falling through a 710 µm sieve of 0.8%, a fraction of 710–850 µm of 93.6% and a fraction remaining on a 850 µm sieve of 5.6%, and a density as measured on 20 granules of 1.432 g/cm$^3$ at the maximum and 1.401 g/cm$^3$ at the minimum (the difference between the maximum and the minimum densities was 0.031 g/cm$^3$).

EXAMPLE 6

Substantially the same procedure as in Example 2 was conducted, except that 680 ml of water-containing ethanol was sprayed over 30 min., thereby producing spherical granules. The water content of the spherical granules at the end of the granulation process was 76.3% based on the plastic limit of the powder materials. The rate of spraying water was 1.13% based on the plastic limit of the powder materials per min.

The resultant spherical granules had a fraction falling through a 180 µm sieve of 3.6%, a fraction of 180–212 µm of 78.4% and a fraction remaining on a 212 µm sieve of 18.0%, and a density as measured on 20 granules of 1.479 g/cm$^3$ at the maximum and 1.452 g/cm$^3$ at the minimum (the difference between the maximum and the minimum densities was 0.027 g/cm$^3$). These granules were further put through a 212 µm sieve to remove the fraction remaining on the sieve. Because the amount of the fraction remaining on the 212 μm sieve was a little, the sieving could be performed efficiently. The density of the spherical granules falling through the sieve was 1.480 g/cm$^3$ at the maximum and 1.459 g/cm$^3$ at the minimum (the difference between the maximum and the minimum densities was 0.021 g/cm$^3$).

EXAMPLE 7

To a powder mixture of 334 g of indomethacin (the measured plastic limit value: 0.63g/cm$^3$), 800 g of AVICEL® PH-101, supra, and 866 g of lactose was added 1000 ml of water. The resultant mixture was kneaded for 20 min. in a kneader (at this point in time, the water content was 74.1% based on the plastic limit of the powder materials). The resultant wet powder materials (2000 g) were charged into a centrifugal fluidized granulator CF-360 Model and then 400 ml of water-containing ethanol having an ethanol content of 30% by weight was sprayed thereonto over 20 min. while rotating the rotary disk at 200 RPM. The resultant powder materials had a water content of 104.1% based on the plastic limit of the powder materials. Therefore, the rate of spraying water to the powder materials was 1.50% based on the plastic limit of the powder materials per min. The spherical granules thus obtained were subjected to tray drying. The dried spherical granules had a fraction falling through a 710 μm sieve of 1.9%, a fraction of 710–850 μm of 93.0% and a fraction remaining on a 850 μm sieve of 5.1%, and a density as measured on 20 granules of 1.415 g/cm$^3$ at the maximum and 1.381 g/cm$^3$ at the minimum (the difference between the maximum and the minimum densities was 0.034 g/cm$^3$).

The resultant spherical granules showed an indomethacin content of 16.5%.

For preparation of a capsule containing 25 mg of indomethacin, it was required to fill 0.152 g of the spherical granules into a capsule. This amount of the spherical granules could be filled to a No.5 capsule (4.5 mmφ×11.0 mm).

COMPARATIVE EXAMPLE 6

Substantially the same procedure as in Example 4, except that a powder mixture of 250 g of indomethacin, 500 g of cornstarch and 200 g of lactose was spread to 1 kg of a commercially available product NONPAREIL® 103 with a grain size of 710–850 μm (the grain size was previously controlled as such by sieving; this product had a fraction falling through a 710 μm sieve of 1.5%, a fraction of 710–850 μm of 98.1% and a fraction remaining on a 850 μm sieve of 0.4%, and a density as measured on 20 granules of 1.547 g/cm$^3$ at the maximum and 1.492 g/cm$^3$ at the minimum; the difference between the maximum and the minimum densities was 0.055 g/cm$^3$), thereby producing indomethacin-coated spherical granules. The resultant spherical granules had an indomethacin content of 12.1%.

For preparation of a capsule containing 25 mg of indomethacin, it was required to fill 0.207 g of the spherical granules into a capsule. Since this amount of the spherical granules could not be filled to a No.5 capsule, a No.4 capsule (5 mmφ×14 mm) was required for filling.

EXAMPLE 8

To the spherical granules (1 gk) prepared by the procedure of Example 1 were charged into a centrifugal fluidized granulator CF-360 Model, and then 340 g of a 5% aqueous solution of hydroxypropyl cellulose HPC-L (Nippon Soda Co., Ltd.) was sprayed thereonto over 60 min. while rotating the rotary disk at 200 RPM and spreading a power mixture of 100 g of acetaminophen and 580 g of the above-defined lactose, thereby preparing an acetaminophen-coated spherical granules.

The resultant spherical granules had a fraction remaining on a 600 μm sieve of 10.1%, a fraction of 500–600 μm of 89.5% and a fraction falling through a 500 μm sieve of 0.4%, thus showing a sharp grain size distribution. The spherical granules of the 500–600 μm fraction had an acetaminophen content of 5.68%.

Subsequently, 1 kg of the spherical granules were charged into a hopper as shown in FIG. 1, and determined on the time-dependent variation of the acetaminophen content of the granules flowing out of the hopper through the discharging port provided at the lower part of the hopper. The results are shown in Table 1 below.

COMPARATIVE EXAMPLE 7

Substantially the same procedure as in Example 8 was conducted, except that a commercially available product NONPAREIL® 103 with a grain size of 355–500 μm was used, thereby producing acetaminophen-coated spherical granules. The resultant spherical granules had a fraction remaining on a 600 μm sieve of 25.6%, a fraction of 500–600 μm of 51.6% and a fraction falling through a 500 μm sieve of 22.8%. The fraction of 500–600 μm had an acetaminophen content of 5.70%, and the fraction falling through a 500 μm sieve had an acetaminophen content of 5.01%.

Using 1 kg of the resultant spherical granules, the time-dependent variation of the acetaminophen content of the spherical granules flowing out of the hopper was determined in the same manner as in Example 8. The results are also shown in Table 1 below.

As shown in Table 1, it is found that the coated spherical granules of the present invention showed an extremely small degree of segregation when they passed through a hopper.

TABLE 1

|  | Example 8 | Com. Example 7 |
|---|---|---|
| Drop rate | 30 g/min. | 23 g/min. |
| Acetaminophen content | 5.7% at 5 min. | 5.7% at 10 min. |
|  | 5.7% at 10 min. | 5.6% at 20 min. |
|  | 5.7% at 20 min. | 5.4% at 30 min. |
|  | 5.7% at 30 min. | 5.6% at 40 min. |
| Average | 5.68% | 5.55% |
| Standard deviatin | 0.0288 | 0.1354 |
| CV value | 0.0050 | 0.0243 |

INDUSTRIAL APPLICABILITY

As described above, the spherical granules of the present invention show an extremely small degree of segregation when they pass through a hopper and have a uniform grain size as well as uniform density. The spherical granule pharmaceutical preparation comprising the spherical granules can diffuse the medicinal ingredient at a relatively constant rate and a large amount of medicinal ingredient can be incorporated to the spherical granules of uniform grain size. Therefore, it becomes possible to design a small volume of capsule dosage form that comprises the spherical granules filled therein.

That is, according to the present invention, the release of the medicinal ingredient from, for example, a pharmaceutical preparation of oral dosage form can be controlled properly and, as a result, the efficacy of the pharmaceutical preparation can also be improved.

What is claimed is:

1. Spherical granules comprising one or more kinds of pharmaceutical substances, which have a mean grain size of from 100 to 1000 μm, wherein at least 90% by weight of the total amount of the spherical granules has such a grain size distribution that the maximum grain size is not larger than 1.2 times the minimum grain size, and wherein the difference in density between the individual spherical granules is less than 0.05 g/cm$^3$.

2. The spherical granules as claimed in claim 1, wherein the pharmaceutical substances are comprised of only non-medicinal ingredients.

3. The spherical granules as claimed in claim 1, wherein the pharmaceutical substances contain a medicinal ingredient.

* * * * *